United States Patent [19]

Armstead

[11] Patent Number: 4,772,281
[45] Date of Patent: Sep. 20, 1988

[54] PATIENT UNDERPAD

[76] Inventor: Kenneth W. Armstead, P.O. Box 598, Lebanon, Tenn. 37087

[21] Appl. No.: 922,955

[22] Filed: Oct. 24, 1986

[51] Int. Cl.[4] .......................................... A61F 13/16
[52] U.S. Cl. .................................. 604/358; 604/378; 604/383
[58] Field of Search ............... 604/358, 372, 378, 383, 604/384, 385.1; 428/284, 286–288, 319.9

[56] References Cited

U.S. PATENT DOCUMENTS

| | | | |
|---|---|---|---|
| 2,515,737 | 7/1950 | Schwarzberger | 604/378 |
| 3,720,212 | 3/1973 | Kaupin | 604/378 |
| 3,989,867 | 11/1976 | Sisson | 428/138 |
| 4,128,686 | 12/1978 | Kyle et al. | 604/383 |
| 4,216,774 | 8/1980 | Graber | 604/372 |
| 4,224,376 | 9/1980 | Ishige et al. | 428/319.9 |
| 4,275,105 | 6/1981 | Boyd et al. | 604/372 |
| 4,454,191 | 6/1984 | von Blücher et al. | 428/287 |
| 4,499,131 | 2/1985 | Knox | 428/126 |
| 4,516,975 | 5/1985 | Mitchell | 604/385.2 |
| 4,551,144 | 11/1985 | Graber | 604/378 |
| 4,603,074 | 7/1986 | Pate et al. | 428/287 |
| 4,664,959 | 5/1987 | Dagenais et al. | 428/192 |
| 4,695,334 | 9/1987 | Mays | 428/286 |

Primary Examiner—C. Fred Rosenbaum
Assistant Examiner—Sharon Rose
Attorney, Agent, or Firm—Mark J. Patterson

[57] ABSTRACT

An absorbent re-usable patient underpad is formed of five layers of fabric consisting from top to bottom of: a absorbent rayon-polyester blend, non-woven polyester; vinyl; and polyester, a synthetic taffeta. The third, fourth and fifth layers are bonded together as are, generally, the first and second layers.

4 Claims, 1 Drawing Sheet

PATIENT UNDERPAD

BACKGROUND OF THE INVENTION

The present invention relates to a re-usable absorbent pad for use in hospitals and nursing homes beneath patients who are incontinent or who might otherwise have the need for an absorbent and protective component of their bedding.

The problem of incontinence in seriously ill or elderly patients at home, in hospitals, and in nursing homes is well recognized by health care professionals. Many products have been developed and marketed for use in protecting patients' bedding from damage caused by absorption of urine and other fluids. Minimizing patient irritation and discomfort caused by prolonged exposure to absorbed fluids is also a concern of those caring for the patient.

Disposable underpads are currently used by many institutions but are relatively expensive and do not provide optimum comfort and absorption because of the types of materials that must be used. Re-usable underpads previously known in the industry suffer from a number of drawbacks. The most significant problem in re-usable pads currently available is durability, that is, ability to withstand exposure to the soap, bleach, and high temperatures of wash and dry cycles. Currently available pads will suffer significant breakdown after one hundred (100) washings or less. Wrinkling of the pads over time is also a problem. The pad disclosed by the present invention will successfully stand up to three hundred (300) washings or more. Similarly, the various combinations of materials and bonding techniques used in the prior art have not resulted in optimum texture on both the top and bottom external surfaces. This provides less comfort to the patient and makes it more difficult in turning the patient because the bottom surface does not allow the pad to slide easily on the bedding.

SUMMARY OF THE INVENTION

According to one embodiment of the present invention, a washable and re-usable patient underpad is formed of five (5) separate layers of fabric: a top layer (patient-contact) of woven polyester or polyester tricot mesh; a second layer (bonded to the first) of a rayon-polyester needle-punch blend; a third layer of non-woven polyester; a fourth layer, bonded to the third, of waterproof vinyl; and a fifth and bottom layer, bonded to the fourth, of nylon or polyester taffeta. All five (5) layers are then stitched together around the top and bottom outside edges. This novel combination of fabrics and bonding overcomes the disadvantages and problems of the prior art.

The top layer of woven polyester or polyester tricot mesh, when glued to the second layer of fabric is smoother and more comfortable to the patient than quilted fabrics now commonly used and withstands dryer heat and bleach better than cotton or nylon. A synthetic sheepskin of polyester-acrylic blend, not bonded to the second layer, is also suitable.

The second layer of rayon-polyester needle-punch blend is the "soaker" or primary fluid absorbent layer. Rayon is an excellent absorbent material. The polyester acts as a stabilizer for the rayon which will not hold up as well if unblended. By bonding this layer to the top layer of fabric, wrinkling of the pad is minimized. It is also a faster drying fabric combination than many "soaker" fabrics used in the prior art.

The third layer of non-woven polyester adds strength to the pad for durability in repeated washings and, by bonding this layer to the vinyl below it, the vinyl is protected from bonding to itself when exposed to the high temperature of commercial dryers. It also holds up to heat and bleach better than nylon.

The fourth layer of PVC vinyl serves as a liquid barrier between the soaker layer and the bedding. It will last longer and is easier to work with during manufacturing than rubber and similar fabrics.

The bottom layer of polyester or nylon taffeta is so closely wound it is almost waterproof. This minimizes the effects of the detergent on the vinyl layer. It is also smoother than fabrics now commonly used as the bottom layer for underpads. This makes it easier to slide the pad on the bedding when moving or turning the patient. For even greater durability with a slightly coarser surface, warp-knit polyester can be used.

The principle object of the present invention, then, is to provide a re-usable patient underpad which is suitable for use in nursing homes, hospitals, and other institutions in the care of incontinent patients.

A further object of the invention is to provide a reusable underpad which can withstand numerous wash and dry cycles with a minimum of damage to and wrinkling of the pad.

Another object of the present invention is to provide a re-usable underpad which can be washed and dried commercially at least two to three hundred times before it must be replaced.

Another object of the present invention is to provide a underpad which will absorb and hold larger amounts of fluid while minimizing discomfort to the patient and while protecting the surrounding environment from damage.

Another object of the present invention is to provide an absorbent underpad which will dry quickly after washing.

A further object of the present invention is to provide smooth top and bottom surfaces for patient comfort and for ease in moving the patient on the bed.

DETAILED DESCRIPTION OF THE PREFERRED EMBODIMENT

Figure 1:
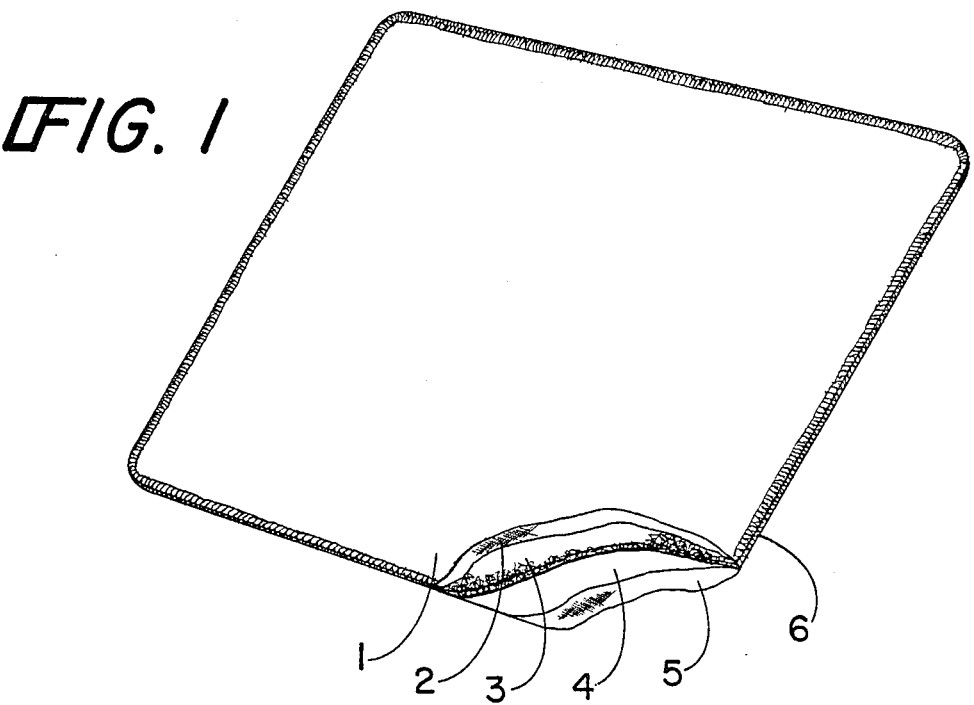
FIG. 1 is a perspective view of the underpad with a partial cutaway and cross section showing the various fabric layers.

While the size and thickness of the pad can vary according to the precise needs of the user, the preferred embodiment shown in the drawings demonstrate the novel combination of fabrics and bonding which give the present invention its advantages in durability, comfort, and ease of use.

Figure 2:
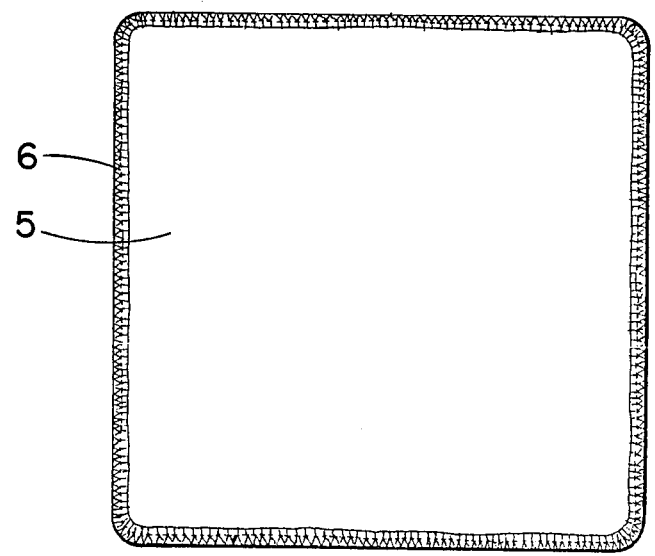
FIG. 2 is a bottom view of the pad showing the smooth bottom layer and the stitching around the edges of the pad.

As shown if FIGS. 1 and 2, the underpad is formed of a top layer 1 of woven polyester or polyester tricot mesh or polyester-acrylic sheepskin, to provide a smooth and comfortable surface for the patient. A second layer 2 of rayon-polyester needle-punch blend is glued to layer 1 across their entire top and bottom surfaces respectively, unless sheepskin is used. The thickness of fabric layer 2 is chosen to accomodate the desired absorption needs of the pad.

Beneath layer 2 is fabric layer 3 of non-woven polyester which is not bonded to layer 2. Bonded across the lower surface of layer 3, by heat or glue, is the water barrier layer 4 of PVC vinyl or similar material. The bottom layer 5 is bonded by glue or heat across the bottom surface of layer 4. The bottom layer 5, which in use contacts the bedding, is made of nylon or polyester taffeta to provide a smooth slideable surface for ease of moving or turning the patient while on the underpad.

All five fabric layers are bound together by stitching 6 around the top and bottom outside edges.

What I claim is:

1. A re-usable patient underpad comprising:
   (a) a top layer of polyester fabric;
   (b) a second absorbent layer of a rayon-polyester blend fabric below and bonded to said top layer;
   (c) a third layer of non-woven polyester fabric;
   (d) a fourth layer of water impervious vinyl fabric below, and bonded to said third layer;
   (e) a fifth and bottom layer of washable synthetic fabric having a smooth bottom surface, said fifth layer below and bonded to said fourth layer; where said five fabric layers are joined together around their outside edges.

2. The underpad of claim 1, where said top layer of fabric is woven polyester.

3. The underpad of claim 1 where said top layer of fabric is polyester tricot mesh.

4. A re-usable patient underpad comprising:
   (a) a top layer of synthetic sheepskin fabric of blended polyester and acrylic;
   (b) a second absorbent layer of rayon-polyester blend fabric, below said top layer;
   (c) a third layer of non-woven polyester fabric;
   (d) a fourth layer of water impervious vinyl fabric, below and bonded to said third layer;
   (e) a fifth and bottom layer of washable synthetic fabric having a smooth bottom surface, said fifth layer below and bonded to said fourth layer; where said five fabric layers are joined together around their outside edges.

* * * * *